United States Patent [19]
Xia

[11] Patent Number: 5,846,774
[45] Date of Patent: Dec. 8, 1998

[54] CHLORELLA VIRUS PROMOTERS

[75] Inventor: Yuannan Xia, Lincoln, Nebr.

[73] Assignee: BioNebraska, Inc., Lincoln, Nebr.

[21] Appl. No.: 821,559

[22] Filed: Mar. 21, 1997

[51] Int. Cl.[6] .............................. C12P 21/06; C12N 1/00; C12N 1/21; C12N 15/11

[52] U.S. Cl. .................. 435/69.1; 435/243; 435/252.33; 435/320.1; 435/325; 435/410; 536/23.1; 536/23.2; 536/23.5; 536/23.51; 536/24.1

[58] Field of Search .................................. 536/23.1, 24.1, 536/23.51, 23.2, 23.5; 435/320.1, 325, 410, 243, 252.3, 252.33, 69.1

[56] References Cited

U.S. PATENT DOCUMENTS

| | | | |
|---|---|---|---|
| 4,952,496 | 8/1990 | Rosenberg et al. | 435/91.41 |
| 5,436,128 | 7/1995 | Harpold et al. | 435/6 |
| 5,563,328 | 10/1996 | Mitra et al. | 800/250 |
| 5,595,887 | 1/1997 | Coolidge et al. | 435/69.7 |

OTHER PUBLICATIONS

DeBoer, et al. *Proc. Nat'l. Acad. Sci. USA*, 80:21–25, (Jan. 1983), "The tac promoter: A functional hybrid derived from the trp and lac promoters".

Gruber, et al. 1993, "Vectors for Plant Transformation", In: *Methods in Plant Molecular Biology and Biotechnology*, Glick and Thompson, eds., CRC Press, Inc. Boca Raton, pp. 89–119.

Horsch, et al. *Science*, 227:1229–31, (Mar. 8, 1985), "A Simple and General Method for Transferring Genes into Plants".

Itakura, et al. *Science*, 198:1056–1063, (Dec. 9, 1977), "Expression in *Escherichia coli* of a Chemically Synthesized Gene for the Hormone Somatostatin".

Lu, et al. *Virology*, 206:339–352, (1995), "Analysis of 45 kb of DNA Located at the Left End of the Chlorella Virus PBCV–1 Genome".

W. R. McClure *Ann. Rev. Biochem.* 54:171–204, (1985), "Mechanism and Control of Transcription Initiation in Prokaryotes".

Miki, et al. 1993, "Procedure for Introducing Foreign DNA into Plants", In: *Methods in Plant Molecular Biology and Biotechnology*, Glick and Thompson, eds., CRC Press, Inc. Boca Raton, pp. 67–88.

Mitra, et al. *Plant Molecular Biology* 26:85–93 (May 1994), "The Chlorella virus adenine methyltransferase gene promoter is a strong promoter in plants".

Narva, et al. *Nucleic Acids Research* 15(23):9807–9823 (1987), "Molecular cloning and characterization of the gene encoding the DNA methyltransferase, M. CviBIII, from Chlorella virus NC–1A".

M. C. O'Neill *The Journal of Biological Chemistry*, 264(10):5522–5530 (Apr. 5, 1989), "*Escherichia coli* Promoters".

Stefan, et al. *Nucleic Acids Research*, 19(2):307–311 (1991), "Molecular cloning and characterization of the gene encoding the adenine methyltransferase M.CviRI from Chlorella virus XZ–6E".

Swaminathan, et al. *Nucleic Acids Research*, 24(13):2463–2469 (May 14, 1996), "Molecular cloning of the three restriction endonuclease R.CviJI form eukaryotic Chlorella virus IL–3A".

Van Etten, et al. *Gene*, 74:113–115 (Jun. 20, 1988), "Chlorella viruses code for restriction and modification enzymes".

Van Etten, et al. *Microbiological Reviews*, 55(4):586–620 (Dec. 1991), Viruses and Viruslike Particles of Eukaryotic Algae.

Van Etten *Mol. Cells*, 5(2):99–106 (1995), "Giant Chlorella Viruses".

Xia, et al. *Molecular and Cellular Biology*, 6(5):1430–1439, "Restriction Endonuclease Activity Induced by PBCV–1 Virus Infection of a Chlorella–Like Green Alga".

Xia, et al. *Molecular and Cellular Biology*, 6(5):1440–1445 (May 1986), "DNA Methyltransferase Induced by PBCV–1 Virus Infection of a Chlorella–Like Green Alga".

*Primary Examiner*—Terry A. McKelvey
*Attorney, Agent, or Firm*—Merchant, Gould, Smith, Smith, Edell & Welter

[57] ABSTRACT

The present invention provides novel promoter sequences obtained from Chlorella virus. The invention includes gene constructs comprising a promoter sequence of the invention operably linked to a DNA sequence encoding a structural gene. The invention also provides vectors and host cells for expressing a product encoded by the structural gene of a gene construct of the invention and cells transformed with the heterologous gene operably linked to the promoter.

19 Claims, 4 Drawing Sheets

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 358 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:1:

```
CCCGGGGATC GCAGGGCATG GGCATTAAAA GAACTTTATG GAATCAAAAA TCTTAGTGAA      60
TTTCCACCAC AGGTATATAG TCTTCAGGAC GCTAACGATG ATATCAACGA TTGTATCAAA     120
GGTTATCGTT TGAGGCACTC ATATCAGGTA GTTTCTACAC AGAAACTTGA ACAACGCCTG     180
GGAAAAGATC CTGAGCATAG TAACTTATAT ACTAGCAGAT GTTGTAACGA TGCTTTATAT     240
GAATATGAAT TAGCACAACG ACAACTACAA AAACAACTTG ATGAATTTGA CGAAGATGGG     300
TATGATTTTT TTCAGGCACG TATAAATACA TTAGATCCGT CGACCTGCAG CCAAGCTT      358
```

( 2 ) INFORMATION FOR SEQ ID NO:2:

( i ) SEQUENCE CHARACTERISTICS:
        ( A ) LENGTH: 374 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:2:

```
CCCGGGGATC TAATTCAGGG TGCGAATTTC TTGAACATCA AAGGTCTGTT GGACGTTTTG      60
TGTGCAGCGG TTGCTGATCG CATTGAATCC ATCAATAAAC AGATTGGGGT AAATATCAAA     120
CCCAGTTAGT CGGACATTAG AAGGATTTGT GAGACCACCA CATCCAACGA CACCTAATGG     180
TGTTGTGAAT GATATATTAG AAATGTTACT TATCATTGAT ATTTGCATAA CACCATTTCC     240
CTTTGCTTGA TTTCTACCTA TACTAATTGA TTGTATTGTA GTGCACGCGG CGTACTTACT     300
TGTATTTGCC GTCTCAGACG TGCTTGATAA TAGTGTGGAA CTCGAGTATG ATCCGTCGAC     360
CTGCAGCCAA GCTT                                                      374
```

( 2 ) INFORMATION FOR SEQ ID NO:3:

( i ) SEQUENCE CHARACTERISTICS:
        ( A ) LENGTH: 207 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:3:

```
CCCGGGGATC ATCGAAAGCA ACTGCCGCAT TCGAAACTTC GACTGCCTCG TTATAAAGGT      60
TAGTGAAAGC CATTGTATGT TATTACTGAG TTATTTAATT TAGCTTGCTT AAATGCTTAT     120
CGTGTTGATA TGATAAATGA CAAATGATAC GCTGTATCAA CATCTCAAAA GATTAATACG     180
AAGATCCGTC GACCTGCAGC CAAGCTT                                         207
```

( 2 ) INFORMATION FOR SEQ ID NO:4:

( i ) SEQUENCE CHARACTERISTICS:
        ( A ) LENGTH: 317 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:4:

```
CCCGGGGATC  GTTTCTCAGG  GCGTCCGGGA  GCATATTTCA  GACTTGTCCA  GCCGTATGAG    60
CATCACGTGC  GCGTTCCTAG  CAAGAGCGTG  TACGTATATT  CTTTCGCTCT  AGAAGATGCA   120
GATTCGAGAC  AACCGAATGG  ATCGAATCTA  TTTGTACCCC  GATATATATA  GAATCTAGTC   180
TAAACAAAAC  GACCGCGGCT  CTTGCCAATA  AATGTGACGC  AATTAACGCA  TTCGTGAATG   240
ATGACTTGTC  CGCCCCGGTT  CTTGACATTC  TAAAAAAATG  TGGAGTATCC  TCGATCCGTC   300
GACCTGCAGC  CAAGCTT                                                     317
```

( 2 ) INFORMATION FOR SEQ ID NO:5:

( i ) SEQUENCE CHARACTERISTICS:
        ( A ) LENGTH: 277 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:5:

```
CCCGGGGATC  TGCGTATTGC  GGGACTTTTG  AGCATTTTCC  AGAACGGATT  GCCGGGACGT    60
ATACTGAACC  TCCAGTCCCT  TTGCTCGTCG  TATTTCCCAT  AATATACATA  TACACTATTT   120
TAATTATTTA  CACCGGTTGT  TGCTGAGTGA  TACAATGCAA  ATTCCCTCCA  CCGAGGAGGA   180
TCGCGAACTG  TCCAAATGTC  TTCTTTCTGC  AGCTCCATAC  GGAGTCGTTA  GGAAACATTC   240
ACTTAATTAT  AGGATCCGTC  GACCTGCAGC  CAAGCTT                              277
```

( 2 ) INFORMATION FOR SEQ ID NO:6:

( i ) SEQUENCE CHARACTERISTICS:
        ( A ) LENGTH: 181 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:6:

```
CCCGGGGATC  AGGCCTCGCT  TATAAATATG  GTATTGATGT  ACTTGCCGGT  GTGATTGACT    60
CAGATTACAG  AGGAGAGTTG  AAAGCAATCC  TTTACAATAC  TACAGAACGT  GACTATATTA   120
TCAAAAAAGG  CGATCAGCCA  AGCTTCGTCG  ACCTGCGATC  CGTCGACCTG  CAGCCAAGCT   180
T                                                                       181
```

( 2 ) INFORMATION FOR SEQ ID NO:7:

( i ) SEQUENCE CHARACTERISTICS:
        ( A ) LENGTH: 316 base pairs
        ( B ) TYPE: nucleic acid
        ( C ) STRANDEDNESS: single
        ( D ) TOPOLOGY: linear     ( i i ) MOLECULE TYPE: cDNA ( x i ) SEQUENCE DESCRIPTION: SEQ ID NO:7:

| | | | | | |
|---|---|---|---|---|---|
| CCCGGGGATC | GCAAAACTCA | CAGTCAACAA | ACCAAAACAC | GGAATGAAGA | AAGGAGAAAC | 60
| TGTGATCATG | TGGCAACAAG | ATGGAGGTGT | CATAGACTAC | ATTTACCCTC | CCTCTGATCA | 120
| TCGAAAGCAA | CTGCCGCATT | CGAAACTTCG | ACTGCCTCGT | TATAAAGGTT | AGTGAAAGCC | 180
| ATTGTATGTT | ATTACTGAGT | TATTTAATTT | AGCTTGCTTA | AATGCTTATC | GTGTTGATAT | 240
| GATAAATGAC | AAATGATACG | CTGTATCAAC | ATCTCAAAAG | ATTAATACGA | AGATCCGTCG | 300
| ACCTGCAGCC | AAGCTT | | | | | 316

( 2 ) INFORMATION FOR SEQ ID NO:8:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:8:

GGGAAATGAG CTGTTGACAA TTAATCATGG CTCGTATAAT GTGTGGAAGC TT    52

( 2 ) INFORMATION FOR SEQ ID NO:9:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:9:

CCCTTTACTC GACAACTGTT AATTAGTAGC CGAGCATATT ACACACCTTC G    51

( 2 ) INFORMATION FOR SEQ ID NO:10:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:10:

CAAAAACAAC TTGATGAATT TGACGAAGAT GGGTATGATT TTTTTCAGGC    50

( 2 ) INFORMATION FOR SEQ ID NO:11:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:11:

TCAGACGTGC TTGATAATAG TGTGGAACTC GAGTATGATC CGTCGACCT    49

( 2 ) INFORMATION FOR SEQ ID NO:12:

( i ) SEQUENCE CHARACTERISTICS:
        ( A ) LENGTH: 48 base pairs
        ( B ) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:12:

GCTTATCGTG TTGATATGAT AAATGACAAA TGATACGCTG TATCAACA      48

( 2 ) INFORMATION FOR SEQ ID NO:13:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:13:

GCCCCGGTTC TTGACATTCT AAAAAAATGT GGAGTATCCT CGATCCGTCG A      51

( 2 ) INFORMATION FOR SEQ ID NO:14:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:14:

ATTTTAATTA TTTACACCGG TTGTTGCTGA GTGATACAAT GCAAATTCCC T      51

( 2 ) INFORMATION FOR SEQ ID NO:15:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:15:

AAAGCAATCC TTTACAATAC TACAGAACGT GACTATATTA TCAAAAAGG      50

( 2 ) INFORMATION FOR SEQ ID NO:16:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:16:

ACTGCCTCGT TATAAAGGTT AGTGAAAGCC ATTGTATGTT ATTACTGAGT T      51

( 2 ) INFORMATION FOR SEQ ID NO:17:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear     ( i i ) MOLECULE TYPE: cDNA -continued ( x i ) SEQUENCE DESCRIPTION: SEQ ID NO:17:

CACCCCAGGC TTTACACTTT ATGCTTCCGG CTCGTATGTT GTGTGGAATT     50

( 2 ) INFORMATION FOR SEQ ID NO:18:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:18:

CACCCCAGGC TTTACACTTT ATGCTTCCGG CTCGTATAAT GTGTGGAATT     50

( 2 ) INFORMATION FOR SEQ ID NO:19:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:19:

AAATGAGCTG TTGACAATTA ATCATCGAAC TAGTTAACTA GTACGCAAGT     50

( 2 ) INFORMATION FOR SEQ ID NO:20:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:20:

AAATGAGCTG TTGACAATTA ATCATCGGCT CGTATAATGT GTGGAATT      48

( 2 ) INFORMATION FOR SEQ ID NO:21:

( i ) SEQUENCE CHARACTERISTICS:
    ( A ) LENGTH: 49 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:21:

TCTGGCGGTG TTGACATAAA TACCACTGGG GGTGATACTG AGCACATCA     49

CHLORELLA VIRUS PROMOTERS

FIELD OF THE INVENTION

This invention relates to novel promoters isolated from Chlorella virus. The novel promoters are useful for expression of heterologous genes in host cells.

BACKGROUND OF THE INVENTION

Genetic engineering allows for isolation of a structural gene from one organism and expression of that gene in a different organism. Expression of a gene includes both transcription of the nucleic acid into mRNA and translation of the mRNA into protein. In order for the structural gene to be expressed in a new organism, the gene must be linked to a regulatory sequence in the proper location to signal transcription of the gene. The regulatory sequence generally includes a promoter sequence upstream from the structural gene. A promoter sequence is a DNA sequence which directs transcription of a structural gene. The nucleic acid sequence of the structural gene is transcribed into messenger RNA (mRNA) and then translated into a sequence of amino acids characteristic of a specific polypeptide or protein. Typically, a promoter sequence is located in the 5' region of a gene, upstream from the transcriptional start site of the structural gene.

A promoter may be inducible or constitutive. In response to an inducing agent, the activity of an inducible promoter is increased, thereby increasing the rate of transcription of an operably linked coding sequence. In contrast, the rate of transcription of a gene under control of a constitutive promoter is not regulated. It is noted, however, that a constitutive promoter can be made an inducible promoter by the addition of an operator sequence. For example, the lac operator is added to the T7 bacteriophage promoter, changing it from a constitutive promoter to one induced by IPTG (Rosenberg, et al., U.S. Pat. No. 4,952,496).

Although not under the control of an inducing agent, some constitutive promoters provide higher levels of transcription than others. High activity promoters providing of high levels of gene transcription can have significant advantage in commercial production of a gene product.

In general, the ability of a promoter to direct transcription outside of its natural host varies. Moreover, the transcription rate of a particular promoter can also vary with the particular host in which the promoter is functioning. Therefore, new promoters capable of promoting high levels of transcription in a wide variety of host cells are needed.

The Chlorella viruses are a group of viruses which infect certain strains of unicellular, eukaryotic, Chlorella-like green algae. (Van Etten, 1995, *Mol. Cells.* 5:99–106; Van Etten, et al., 1991, *Microbiol. Rev.* 55:586–620). These viruses are among the largest and most complex viruses known, generally 150–190 nm diameter polyhedrons containing greater than 300 kb of double stranded DNA. The Chlorella virus genome has the potential to encode several hundred gene products.

Chlorella virus methyltransferase promoters have been isolated and shown to function in prokaryotic and eukaryotic host cell systems. These methyltransferase promoters function well in some bacterial and higher plant cells. See, for example, U.S. Pat. No. 5,563,328; and Mitra, et al., 1994, *Plant Molec. Biol.*, 26: 85–893 ("Mitra").

The present invention provides novel promoter sequences isolated from Chlorella virus that can induce a high level of gene expression in prokaryotic or eukaryotic cells.

SUMMARY OF THE INVENTION

The present invention provides novel promoter sequences isolated from Chlorella virus (SEQ ID NOS: 1–7). The invention includes gene constructs comprising a promoter sequence of the invention operably linked to a DNA sequence of a structural gene. The invention further provides vectors and host cells for expressing a product encoded by the structural gene of a gene construct of the invention, and cells transformed with a heterologous gene operably linked to the promoter.

In one embodiment, the structural gene is a non-Chlorella virus DNA sequence encoding a protein for production in a host cell. According to this embodiment, the non-Chlorella virus DNA sequence can be any suitable structural gene which encodes a peptide, protein, hormone, enzyme, etc. Examples of suitable structural genes include glucagon like peptide 1 (GLP-1), growth hormone releasing factor (GRF), parathyroid hormone (PTH), interlinking peptides, amidation code sequences, carbonic anhydrase, beta-galactosidase, chloramphenicol acetyltransferase (CAT), glutathione acetyltransferase, and the like.

A gene construct of the invention is introduced into an appropriate host cell for expression of the gene product. Host cells are transformed directly or through a vector. In one embodiment, a suitable vector for a prokaryotic cell such as *E. coli* strains HB101 or JM109 is the plasmid pKK232-8.

The invention further provides a process for producing a protein composition. According to this embodiment, a protein product is produced in a host cell transformed with a gene construct of the invention. The gene construct includes a promoter sequence of the invention operably linked to a structural gene encoding the protein to be produced in the host cell. The invention also provides methods for screening and isolating a promoter sequence having strong transcriptional properties, including truncated versions of the Chlorella virus promoters shown below.

DETAILED DESCRIPTION OF THE INVENTION

The present invention is directed to novel nucleic acid sequences isolated from the genome of several Chlorella viruses, which isolated nucleic acid sequences function as transcriptional promoters [SEQ ID NOS: 1–7]. The disclosed promoter sequences are operably linked to a structural gene to direct transcription of the structural gene in prokaryotic or eukaryotic cells. The disclosed promoter sequences provide a high level of gene expression in comparison to native or other non-native promoters, as shown in the examples below in bacterial host cells.

The disclosed promoter sequences are operably linked to a structural gene sequence to form a "gene construct" or "expression cassette". In a typical embodiment, the structural gene sequence of a gene construct will be a heterologous sequence. As used herein, a "heterologous sequence" is a DNA sequence which is different than that to which the promoter sequence is operably linked in the Chlorella virus.

CHLORELLA VIRUS PROMOTER SEQUENCES

The following nucleic acid sequences were isolated from Chlorella viruses and include a promoter sequence for directing transcription of a structural gene.

cvp-1 [SEQ ID NO: 1]
CCCGGGGATC GCAGGGCATG GGCATTAAAA GAACTTTATG GAATCAAAAA
TCTTAGTGAA TTTCCACCAC AGGTATATAG TCTTCAGGAC GCTAACGATG
ATATCAACGA TTGTATCAAA GGTTATCGTT TGAGGCACTC ATATCAGGTA
GTTTCTACAC AGAAACTTGA ACAACGCCTG GGAAAAGATC CTGAGCATAG
TAACTTATAT ACTAGCAGAT GTTGTAACGA TGCTTTATAT GAATATGAAT
TAGCACAACG ACAACTACAA AAACAACTTG ATGAATTTGA CGAAGATGGG
TATGATTTTT TTCAGGCACG TATAAATACA TTAGATCCGT CGACCTGCAG
CCAAGCTT cvp-3 [SEQ ID NO: 2]
CCCGGGGATC TAATTCAGGG TGCGAATTTC TTGAACATCA AAGGTCTGTT
GGACGTTTTG TGTGCAGCGG TTGCTGATCG CATTGAATCC ATCAATAAAC
AGATTGGGGT AAATATCAAA CCCAGTTAGT CGGACATTAG AAGGATTTGT
GAGACCACCA CATCCAACGA CACCTAATGG TGTTGTGAAT GATATATTAG
AAATGTTACT TATCATTGAT ATTTGCATAA CACCATTTCC CTTTGCTTGA
TTTCTACCTA TACTAATTGA TTGTATTGTA GTGCACGCGG CGTACTTACT
TGTATTTGCC GTCTCAGACG TGCTTGATAA TAGTGTGGAA CTCGAGTATG
ATCCGTCGAC CTGCAGCCAA GCTT cvp-6 [SEQ ID NO: 3]
CCCGGGGATC ATCGAAAGCA ACTGCCGCAT TCGAAACTTC GACTGCCTCG
TTATAAAGGT TAGTGAAAGC CATTGTATGT TATTACTGAG TTATTTAATT
TAGCTTGCTT AAATGCTTAT CGTGTTGATA TGATAAATGA CAAATGATAC
GCTGTATCAA CATCTCAAAA GATTAATACG AAGATCCGTC GACCTGCAGC
CAAGCTT cvp-10 [SEQ ID NO: 4]
CCCGGGGATC GTTTCTCAGG GCGTCCGGGA GCATATTTCA GACTTGTCCA
GCCGTATGAG CATCACGTGC GCGTTCCTAG CAAGAGCGTG TACGTATATT
CTTTCGCTCT AGAAGATGCA GATTCGAGAC AACCGAATGG ATCGAATCTA
TTTGTACCCC GATATATATA GAATCTAGTC TAAACAAAAC GACCGCGGCT
CTTGCCAATA AATGTGACGC AATTAACGCA TTCGTGAATG ATGACTTGTC
CGCCCCGGTT CTTGACATTC TAAAAAAATG TGGAGTATCC TCGATCCGTC
GACCTGCAGC CAAGCTT cvp-13 [SEQ ID NO: 5]
CCCGGGGATC TGCGTATTGC GGGACTTTTG AGCATTTTCC AGAACGGATT
GCCGGGACGT ATACTGAACC TCCAGTCCCT TTGCTCGTCG TATTTCCCAT
AATATACATA TACACTATTT TAATTATTTA CACCGGTTGT TGCTGAGTGA
TACAATGCAA ATTCCCTCCA CCGAGGAGGA TCGCGAACTG TCCAAATGTC
TTCTTTCTGC AGCTCCATAC GGAGTCGTTA GGAAACATTC ACTTAATTAT
AGGATCCGTC GACCTGCAGC CAAGCTT cvp-15 [SEQ ID NO: 6]
CCCGGGGATC AGGCCTCGCT TATAAATATG GTATTGATGT ACTTGCCGGT
GTGATTGACT CAGATTACAG AGGAGAGTTG AAAGCAATCC TTTACAATAC
TACAGAACGT GACTATATTA TCAAAAAAGG CGATCAGCCA AGCTTCGTCG
ACCTGCGATC CGTCGACCTG CAGCCAAGCT T cvp-16 [SEQ ID NO: 7]
CCCGGGGATC GCAAAACTCA CAGTCAACAA ACCAAAACAC GGAATGAAGA
AAGGAGAAAC TGTGATCATG TGGCAACAAG ATGGAGGTGT CATAGACTAC
ATTTACCCTC CCTCTGATCA TCGAAAGCAA CTGCCGCATT CGAAACTTCG
ACTGCCTCGT TATAAAGGTT AGTGAAAGCC ATTGTATGTT ATTACTGAGT
TATTTAATTT AGCTTGCTTA AATGCTTATC GTGTTGATAT GATAAATGAC
AAATGATACG CTGTATCAAC ATCTCAAAAG ATTAATACGA AGATCCGTCG
ACCTGCAGCC AAGCTT The gene construct preferably also includes enhancers, markers, polyadenylation sequences or other regulatory nucleic acid sequences. When a secreted protein is to be produced, the coding sequence of the structural gene preferably includes a nucleic acid sequence encoding a signal peptide.

The disclosed gene constructs are used to express a protein product encoded by the structural gene in host cells. The gene construct is incorporated into the host cells directly or via a vector, using known methods. The protein product remains intracellular post-expression or is secreted extracellularly when a nucleic acid sequence encoding a signal peptide is included in the gene construct.

The method by which these new promoter sequences were discovered is described more fully in the Examples below. Briefly, restriction DNA fragments were generated from the viral genomes of five Chlorella viruses, CA-4B, Al-1A, PBCV-1, SC-1A, and NC-1A. (Van Etten, 1991, *Microbiol. Rev.* 55:586–620) The restriction fragments were inserted into plasmid pKK232-8 by a shotgun cloning procedure using known methods (Sambrook, et al., 1989, *Molecular Cloning*).

The plasmid vector pKK232-8 contains a promoterless chloramphenicol acetyltransferase (CAT) gene and multiple cloning sites upstream for insertion of DNA restriction fragments. *E. coli* were then transformed with the cloned pKK232-8 and the transformants carrying promoter sequences were screened for resistance to chloramphenicol. To obtain high activity promoters, chloramphenicol-resistant transformants were further screened using increasing concentrations of chloramphenicol in the growth medium.

As used herein, the "strength" of a promoter refers to the level of transcription directed by the promoter. A "strong" promoter provides a greater level of transcription than a weak promoter. Thus, the phrase "strong promoter" is used interchangeably with a "high activity promoter". Strong promoters are particularly useful for commercial production of a gene product.

It is appreciated that the entire nucleic acid sequence recited for each of SEQ ID NOS: 1–7 may not be required for promoter function. Using the methods described above and in the Examples below, the disclosed promoter sequences can be further restricted, e.g. truncated or modified, and screened to refine the active promoter regions.

PREPARATION OF GENE CONSTRUCTS

According to the invention, a gene construct includes at least one structural gene coding sequence which is operably linked to a transcriptional control region. A transcriptional control region includes promoters, and other regulatory elements, such as enhancers, regulatory elements, polyadenylation sequences, transcriptional initiation regions, and transcriptional termination sequences. SEQ ID NOS: 1–7 each include a promoter sequence and may also include additional regulatory elements. Methods for operably linking a promoter sequence to a structural gene sequence are known and disclosed in, for example, Itakuri, et al., 1977, *Science* 198:1056–1063.

A structural gene of a gene construct according to the disclosure will typically encode a protein or polypeptide product. Any known or later discovered structural gene which encodes a desired product is operably linked to a promoter sequence of the invention using known methods. Examples of known structural genes suitable for use with the promoters of the invention include those nucleic acid sequences encoding: glucagon-like peptide 1 (GLP-1), growth hormone releasing factor (GRF), parathyroid hormone (PTH), carbonic anhydrase, beta-galactosidase, chloramphenicol acetyltransferase (CAT), glutathione acetyltransferase, interlinking peptides, amidation sequences, and the like structural genes.

Therefore, in one embodiment, a promoter sequence of the invention is operably linked to a DNA sequence encoding carbonic anhydrase, for example, human carbonic anhydrase. In another embodiment, a promoter sequence of the invention is linked to a DNA sequence encoding multiple copies of a desired protein. An example of a suitable multiple copy structural gene for glucagon like peptide-1 (GLP-1) is disclosed in U.S. Pat. No. 5,595,887.

GENE TRANSFORMATION METHOD

Once a gene construct is formed, it is introduced into a host cell directly or subcloned into an appropriate vector for transforming a host cell.

Methods of transforming cells are known, and the preferred method varies with the type of host cell to be transformed. As used herein, a "host cell" refers to the cell in which the structural gene of the gene construct is ultimately expressed. For prokaryotic and eukaryotic host cells, including bacterial, yeast, and animal host cells, preferred methods of transformation include methods of freeze/thaw, calcium chloride precipitation, calcium phosphate precipitation, plasmids, protoplast transformation, liposome mediated transformation, electroporation, and other known transformation methods.

For plant cells, preferred methods of transformation include Agrobacterium-mediated transformation, electroporation, microparticle bombardment, protoplast fusion, combinations of these and other known transformation methods.

HOST CELLS

Suitable bacterial host cells for expression of a gene construct of the invention include *Escherichia coli, Bacillus subtilis* and Streptomyces. Plant and animal host cells, including yeast cells, are also useful with the inventive promoters.

Suitable vector systems for carrying the gene constructs into the host cells include, for example, plasmids, viruses, phages, and yeast artificial chromosomes (YAC's). Suitable plasmids for transforming a bacterial host cell with a gene construct of the invention include pKK232-8 or pB0304, as described in the examples below.

Methods for introducing foreign genes into plants are known and can be used to insert a gene construct of the invention into a plant host, including biological and physical plant transformation protocols. See, for example, Miki, et al., 1993, "Procedure for Introducing Foreign DNA Into Plants", In: *Methods in Plant Molecular Biology and Biotechnology,* Glick and Thompson, eds., CRC Press, Inc., Boca Raton, pages 67–88. The methods chosen vary with the host plant, and include chemical transfection methods such as calcium phosphate, microorganism-mediated gene transfer such as Agrobacterium (Horsch, et al., *Science* 227:1229–31, 1985), electroporation, micro-injection, and biolistic bombardment.

Expression vectors and in vitro culture methods for plant cell or tissue transformation and regeneration of plants are known and available. See, for example, Gruber et al., 1993, "Vectors for Plant Transformation: In: *Methods in Plant Molecular Biology and Biotechnology,* Glick and Thompson, eds., CRC Press, Inc., Boca Raton, pages 89–119.

EXAMPLES

The invention is more fully described with reference to the following examples, which are not intended to limit the invention in any way.

EXAMPLE 1

Generating Viral DNA Fragments

Viral DNA extracted from five Chlorella viruses CA-4B; Al-1A; PBCV-1; SC-1A; and NC-1A was provided by Dr. Van Etten at the University of Nebraska. The extracted viral DNA (1.5 $\mu$g of each) was pooled and viral DNA fragments were generated by digestion with Sau3Al (New England Biolabs, Beverly, Mass.) in (100 μl volume) 100 mM NaCl, 10 mM Bis Tris Propane-HCl, 10 mM $MgCl_2$, 1 mM dithiothreitol, and 100 μg/ml BSA. The mixture was incubated at 37° C. for 120 minutes and stopped by 10 mM EDTA. Sau3Al fragments were precipitated from the digestion mixture by ethanol and washed with ethanol.

EXAMPLE 2

Cloning Fragments into pKK232-8

Figure 1:
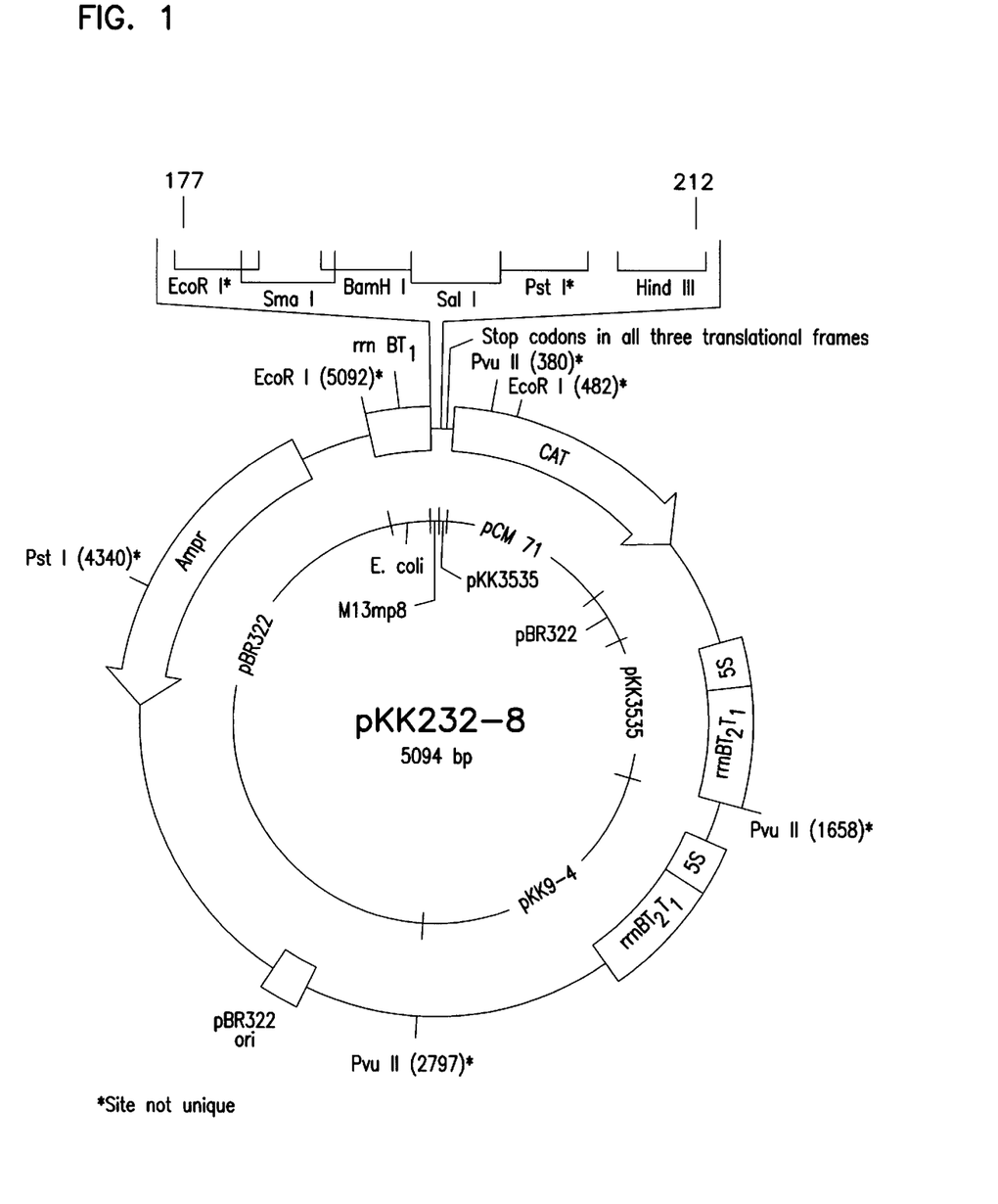
FIG. 1 is a diagrammatic representation of the pKK232-8 plasmid map.

The Sau3Al viral fragments produced as described for Example 1, were cloned into plasmid pKK232-8 at the single BamHI site by a shotgun cloning procedure as described in Sambrook, et al., 1989, *Molecular Cloning*. Plasmid pKK232-8 was purchased from Pharmacia (Piscataway, N.J.). The map of pKK232-8 is diagrammatically represented in FIG. 1. Preparations of DNA, fill-in reaction and ligations were carried out as described in Sambrook et al., supra or according to the manufacturer's directions.

The Chlorella viral DNA fragments were ligated to 1 μg of pKK232-8 which was previously treated with BamHI and calf intestinal alkaline phosphatase (CIP) to yield recombinant plasmids PCVP-1; pCVP-3; pCVP-6; PCVP-10; pCVP-13; pCVP-15; and pCVP-16. The seven Chlorella virus promoters operably linked to a heterologous CAT gene are diagrammatically shown in FIG. 2. (Abbreviations: Sm, SmaI; Sa, SalI H, HindIII; CAT, chloramphenicol acetyltransferase gene), Calf intestinal alkaline phosphatase was purchased from Promega (Madison, Wis.). T4 DNA ligase was purchased from BRL (Rockville, Md.).

pKK232-8 is a derivative of pBR322 which contains promotorless chloramphenicol acyltransferase (CAT) gene and multiple cloning sites upstream for insertion of DNA restriction fragments. *E. Coli* cells transformed with pKK232-8 are resistant to ampicillin but sensitive to chloramphenicol unless a DNA fragment containing a promoter is inserted upstream of the CAT gene to induce expression of CAT. If such a promoter is inserted, cells carrying the recombinant plasmid express CAT and thereby acquire resistance to chloramphenicol.

pKK232-8 is designed to reduce background of chloramphenicol resistance and increase the capacity of screening strong promoters. To reduce background, the CAT gene is flanked by efficient transcription terminators that block transcription into the CAT gene from other promoters present on the plasmid. Translational stop codons are introduced in all three reading frames between the multiple cloning sites and the initiation codon of the CAT gene to prevent translational readthrough from any ATG start codon that might be introduced by the cloned promoter fragment. The CAT gene also contains its own ribosome-binding signal and ATG start codon to allow efficient translation from CAT mRNA.

EXAMPLE 3

Transformation of *E. coli* and Selection of Transformants

Transformation of *E. coli* strains HB101 and JM109 was performed as described by Sambrook, et al., 1989, supra. The *E. coli* strains were purchased from Promega (Madison, Wis.).

Transformed *E. coli* were screened for resistance to ampicillin indicating transformation with pKK232-8, and for resistance to chloramphenicol, indicating insertion of a promoter. The strength of an inserted promoter was estimated by measuring cell growth in the presence of increasing amounts of chloramphenicol.

Positive colonies were isolated on Luria Broth (LB) plates containing 30 μg/ml ampicillin and various concentrations of chloramphenicol (5, 10, 20, 30, 100 μg/ml). *E. coli* colonies which were resistant to 100 μg/ml chloramphenicol were selected and inoculated into LB medium containing 200, 400, 600, 700, 900 μg/ml chloramphenicol. Cell growth was monitored by measuring $OD_{600}$ of cultures.

Several thousand transformants, resistant to 30 μg/ml chloramphenicol, were obtained. The number of transformants resistant to chloramphenicol dramatically decreased with increased concentration of the antibiotic. Only about 500 transformants were resistant to 100 μg/ml chloramphenicol and only 36 transformants showed resistance to 500 μg/ml chloramphenicol. Cells transformed with control pKK232-8 without an inserted promoter were not resistant to chloramphenicol above a concentration of 5 μg/ml.

Figure 2:
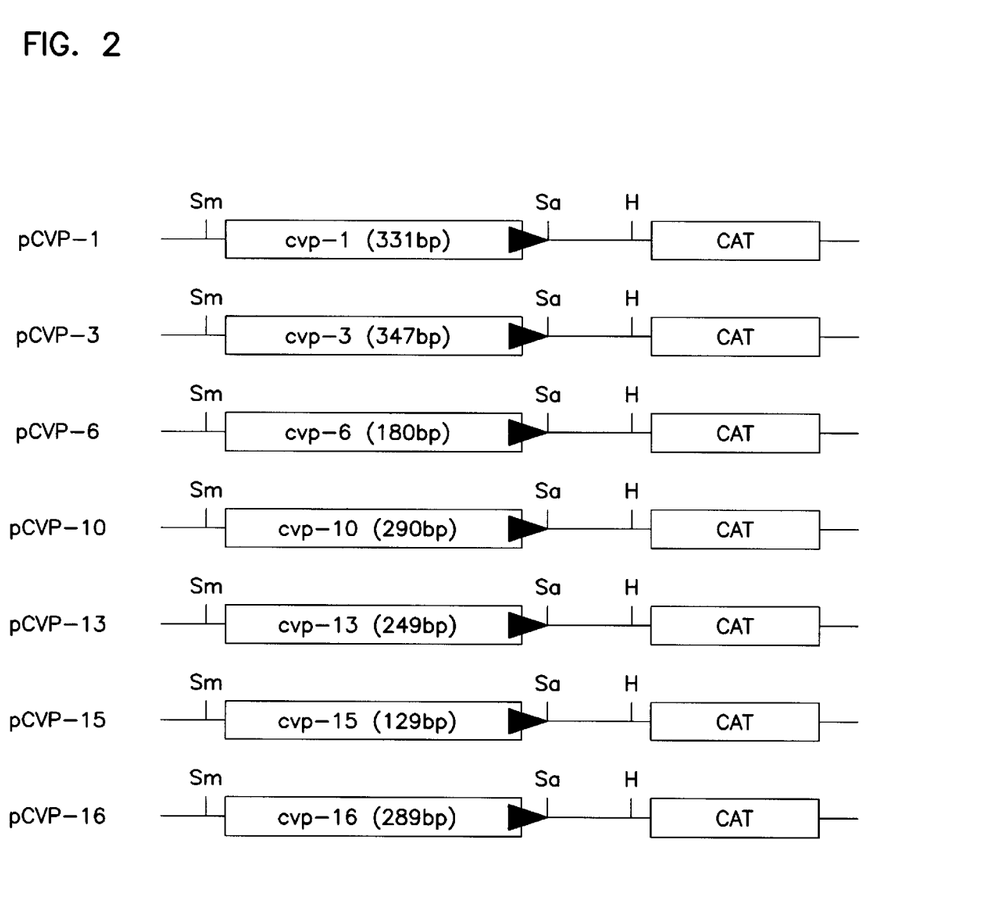
FIG. 2 is a diagrammatic representation of gene constructs using seven Chlorella virus promoters linked to the heterologous DNA sequence encoding the CAT protein.

The 36 transformants that showed a resistance to 500 μg/ml of chloramphenicol were further exposed to 500 μg, 700 μg, and 900 μg/ml chloramphenicol. Seven transformants showed normal growth in LB medium containing 700 μg/ml chloramphenicol and slower growth in the presence of 900 μg/ml chloramphenicol (FIG. 2).

EXAMPLE 4

Comparison of CAT Activity Induced by Chlorella Virus Promoters

Figure 3:
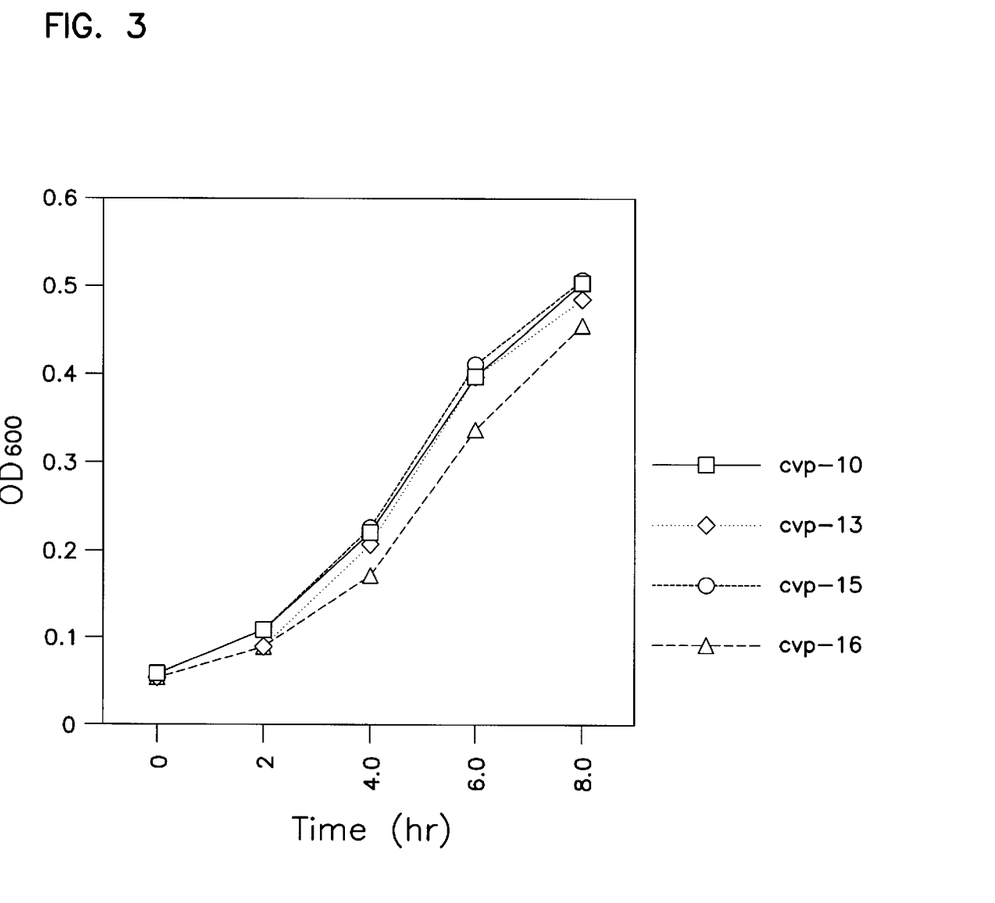
FIG. 3 is a comparison of CAT activities in chloramphenicol-resistant *E. coli* transformed with the CAT gene operably linked to the promoter sequences cvp-10, cvp-13, cvp-15 and cvp-16.

The CAT activity expressed by the chloramphenicol-resistant Chlorella virus promoter transformants of Example 3 was compared. Four of the seven chloramphenicol-resistant *E. coli* transformants, (CVP-10; CVP-13; CVP-15 and CVP-16) were grown in the presence of 600 μg/ml of chloramphenicol. Cell growth was monitored by measuring cell density ($OD_{600}$) at various times. As shown in FIG. 3, the four transformants displayed similar cell growth, indicating that similar levels of CAT activity was expressed in each culture.

EXAMPLE 5

Purification of Plasmid DNA

Plasmid DNA was purified from those colonies showing the highest level of chloramphenicol resistance (700 to 900 μg/ml) using the Wizard miniprep plasmid DNA purification kit (Promega Co., Madison, Wis.) or Qiagen DNA purification kit (Qiagen Inc., Chatsworth, Calif.). Analysis of the plasmids by restriction endonuclease digestion indicated that all plasmids carried a DNA insert fragment.

The plasmids were digested with SmaI and HindIII and electrophoresed on 7.5% polyacrylamide gel or 0.8% agarose gel. The electrophoretic gel showed the seven viral promoter fragments ranged in size from 100 to 400 bp, as shown diagrammatically in FIG. 2.

EXAMPLE 6

Sequencing Promoter Fragments

The seven promoter-containing viral DNA fragments (cvp-1, cvp-3, cvp-6, cvp-10, cvp-13, cvp-15, and cvp-16)

were excised from the pKK232-8 vector with SmaI and HindIII and subcloned into pUC19 or pBluescriptSK(+)II for sequencing. DNA sequencing was performed by the University of Nebraska Lincoln (UNL) sequencing lab using an automatic LICOR sequencer. sequences were determined in both directions using the Sanger dideoxy chain termination method.

Sequence analysis of all seven Chlorella virus fragments revealed Sau3Al sites at each end of the Chlorella virus inserts and flanking the multiple cloning sites of the pKK232-8 vector. The size of the DNA sequence for the seven promoter fragments coincided with the size of the restriction fragments determined by polyacrylamide gel electrophoresis.

| SEQ ID NO: | *Chlorella* Virus DNA Insert |
|---|---|
| 1 | cvp-1 |
| 2 | cvp-3 |
| 3 | cvp-6 |
| 4 | cvp-10 |
| 5 | cvp-13 |
| 6 | cvp-15 |
| 7 | cvp-16 |

Known *E. coli* promoter sequences contain 3 critical elements: two hexamer sequences (−35 region and −10 region) and a 16–18 bp spacing between these two regions. Using lac, lacUV5, trp, tac and PL promoter consensus sequences as references, −35 and −10 region putative sequences were assigned to each of the seven viral promoters. As shown below in Table I these hexamer sequences are either identical to, or only slightly different from, the consensus sequences of the known *E. coli* promoters. For example, the −35 sequence region of cvp-10 (TTGACA) or cvp-15 (TTTACA) is identical to that found in trp (TTGACA) or lac (TATGTT).

Six of the seven isolated viral promoters of the invention have 16–18 bp spacing between the putative −35 and −10 regions. Both the cvp-13 viral promoter and the lac promoter have an identical −35 hexamer sequence (TTTACA), exactly the same spacing (18 bp) between the −35 and −10 regions, and a very similar −10 hexamer sequence (TACAAT for cvp-13 and TATAAT for lac).

EXAMPLE 7

Comparing Promoter Activity of cvp-13 and tac

The tac promoter is a very strong *E. coli* promoter (de Boer, et al., 1983, *Proc. Natl. Acad. Sci.* 80:21–25) that has been widely used for gene expression in both research and industry. To compare promoter activity of viral promoter cvp-13 and promoter activity of tac in the same assay system, a promoter plasmid of tac was constructed using pKK232-8.

Two complementary oligomers containing the tac sequence,

5'-GGGAAATGAGCTGTTGACAATTAATCATGGCTC-GTATAATGTGTGGAAGCTT-3' [SEQ ID NO: 8] and

Figure 4:
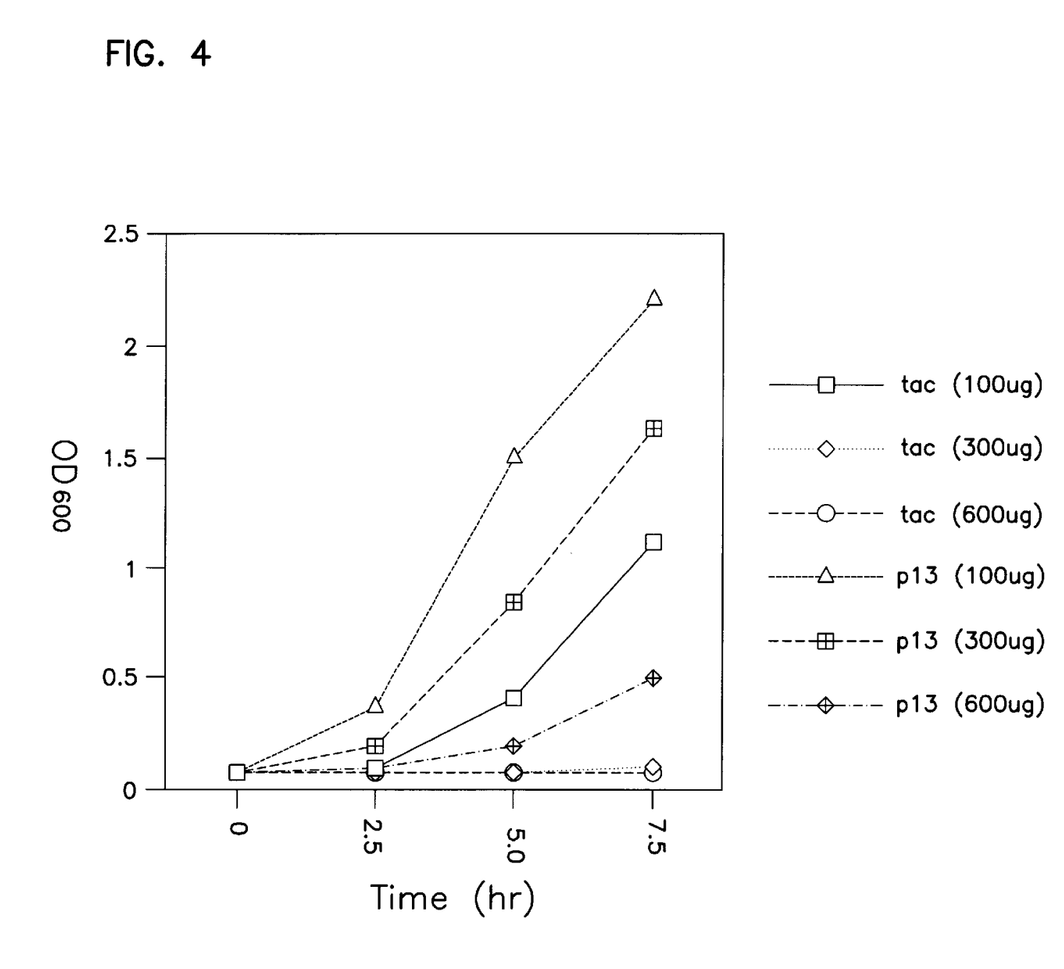
FIG. 4 is a comparison of promoter activities of the Chlorella virus promoter cvp-13 and the tac promoter transformed into *E. coli* HB101 and grown in the presence of varying concentrations of chloramphenicol.

5'-CCCTTTACTCGACAACTGTTAATTAGTAGCCGAG-CATATTACACACCTTCG-3' [SEQ ID NOS: 9]

were annealed and inserted in pKK232-8 upstream of the CAT gene, between SmaI and HindIII. The resulting plasmid, pTAC-cat, was transformed into *E. coli* HB101. Cells containing either pTAC-cat or pCVP-13 were grown in the presence of 100, 300 or 600 μg/ml of chloramphenicol. Antibiotic resistance was monitored by measuring cell growth densities at various times. As shown in FIG. 4, at all three levels of chloramphenicol concentration, the cvp-promoter showed higher promoter activity than the tac promoter.

The above specification, examples and data provide a complete description of the manufacture and use of the composition of the invention. Since many embodiments of the invention can be made without departing from the spirit and scope of the invention, the invention resides in the claims hereinafter appended.

| Promoter consensus | −35 Position TTGACA | −10 Position TATAAT | +position SEQ ID NO: |
|---|---|---|---|
| cvp-1 | CAAAAACAACTTGATGA ATTTGACGAAGATGGGTATGATTTTTTTCAGGC | | 10 |
| cvp-3 | TCAGACGTGCTTGATAATAG TGTGGAACTCGAGTATGATCCG TCGACCT | | 11 |
| cvp-6 | GCTTATCGTGTTGATATGATAAATGACAAAT GATACGCTGTATCAACA | | 12 |
| cvp-10 | GCCCCGGTTCTTGACATTCTAAAAAAATGTGGAGTATCCTCGATCCGTCGA | | 13 |
| cvp-13 | ATTTTAATTATTTACACCGGTTGTTGCTGAGTGATACAATGCAAATTCCCT | | 14 |
| cvp-15 | AAAGCAATCCTTTACAATAC TACAGAACGTGACTATATTATCAAAAAAGG | | 15 |
| cvp-16 | ACTGCCTCGTTATAAAGGTTAGTGAAAGCCATTGTATGTTATTACTGAGTT | | 16 |
| lac | CACCCCAGGCTTTACACTTTATGCTTCCGGCTCGTATGTTGTG TGGAATT | | 17 |
| lacUV5 | CACCCCAGGCTTTACACTTTATGCTTCCGGCTCGTATAATGTG TGGAATT | | 18 |
| trp | AAATGAGCTGTTGACAATTAATCATCGAACTA GTTAACTAGTACGCAAGT | | 19 |
| tac | AAATGAGCTGTTGACAATTAATCAT CGGCTCGTATAATGTG TGGAATT | | 20 |
| PL | TCTGGCGGTGTTGACATAAATACCACT GGGGGTGATACTGAG CACATCA | | 21 |

"A" in bold type indicates the start site of transcription. Abbreviations: lac, the lac promoter; lacUV5, the lacUV5 promoter; trp, the trp promoter; tac, the tac promoter; PL, bacteriophage lamda PL promoter.

What is claimed is:

1. A vector comprising the nucleic acid sequence set forth as SEQ ID NO: 1.
2. A vector comprising the nucleic acid sequence set forth as SEQ ID NO: 2.
3. A vector comprising the nucleic acid sequence set forth as SEQ ID NO: 3.
4. A vector comprising the nucleic acid sequence set forth as SEQ ID NO: 4.
5. A vector comprising the nucleic acid sequence set forth as SEQ ID NO: 5.
6. A vector comprising the nucleic acid sequence set forth as SEQ ID NO: 6.
7. A vector comprising the nucleic acid sequence set forth as SEQ ID NO: 7.
8. A gene construct comprising a promoter operably linked to a heterologous structural gene, said promotor comprising the nucleic acid sequence set forth as SEQ ID NO: 1,2,3,4,5,6,or7.
9. The gene construct of claim 8, wherein said structural gene encodes carbonic anhydrase.
10. The gene construct of claim 9, wherein said carbonic anhydrase is human carbonic anhydrase.
11. The gene construct of claim 8, wherein said structural gene encodes glucagon-like peptide-1, growth hormone releasing factor, or parathyroid hormone.

12. A host cell containing a gene construct comprising a promotor operably linked to a heterologous structural gene, said promotor comprising the nucleic acid sequence set forth as SEQ ID NO: 1, 2, 3, 4, 5, 6, or 7.

13. The host cell of claim 12, wherein said host cell is a prokaryotic cell.

14. The host cell of claim 13, wherein said prokaryotic cell is an *E. coli* cell.

15. The host cell of claim 14, wherein said *E. coli* cell is a HB101 cell or JM109 cell.

16. A process for producing a protein, said process comprising:

transforming a host cell with a gene construct comprising a promotor operably linked to a structure gene, said promotor comprising a nucleic acid sequence set forth as SEQ ID NO: 1,2,3,4,5,6, or 7;and culturing the host cell under conditions whereby the protein is expressed.

17. The process of claim 16, further comprising the step:

isolating the expressed protein from the host cell.

18. A process for producing a protein said process comprising:

incubating a host cell under conditions whereby the protein is expressed, which host cell comprises a gene construct comprising a promotor operably liked to a heterologous nucleic acid sequence encoding the protein, said promoter comprising a nucleic acid sequence as set forth as SEQ ID NO: 1, 2, 3, 4, 5, 6, or 7.

19. The process of claim 18, further comprising the step:

isolating the expressed protein from the host cell.

* * * * *

UNITED STATES PATENT AND TRADEMARK OFFICE
CERTIFICATE OF CORRECTION

PATENT NO. : 5,846,774
DATED : DECEMBER 8, 1998
INVENTOR(S) : XIA

It is certified that error appears in the above-identified patent and that said Letters Patent is hereby corrected as shown below:

Col. 7, line 25: "PCVP-1" should read ---pCVP-1---

Col. 7, line 25: "PCVP-10" should read ---pCVP-10---

Col. 21, line 14, claim 16: "structure" should read ---structural---

Signed and Sealed this

Sixth Day of June, 2000

Q. TODD DICKINSON

*Attest:*

*Attesting Officer*          *Director of Patents and Trademarks*